United States Patent [19]

Smith et al.

[11] Patent Number: 4,912,048
[45] Date of Patent: Mar. 27, 1990

[54] FLUTED CULTURE VESSEL

[75] Inventors: Jerry W. Smith, Ann Arbor; Deborah R. Siena, Willis, both of Mich.

[73] Assignee: Difco Laboratories, Detroit, Mich.

[21] Appl. No.: 136,021

[22] Filed: Dec. 21, 1987

[51] Int. Cl.$^4$ .............................................. C12M 3/00
[52] U.S. Cl. .................................. 435/296; 435/284; 435/287; 435/286; 206/219; 215/1 C; 220/72
[58] Field of Search ............... 435/296, 285, 287, 316, 435/284; 206/219; 215/DIG. 8, DIG. 3, 100 R, 101, DIG. 1; 220/72

[56] References Cited

U.S. PATENT DOCUMENTS

| | | |
|---|---|---|
| 3,532,609 | 2/1968 | Riera . |
| 3,701,717 | 10/1972 | Ingvorsen ........................ 435/296 |
| 3,911,619 | 10/1975 | Dedolph ........................ 435/285 X |
| 3,941,661 | 1/1974 | Noteboom . |
| 4,121,976 | 10/1978 | Gleeson ........................ 435/296 |
| 4,172,013 | 5/1977 | Skoda et al. . |
| 4,242,459 | 11/1978 | Chick et al. . |
| 4,317,885 | 8/1980 | Johnson et al. . |
| 4,514,499 | 2/1983 | Noll . |
| 4,655,035 | 5/1987 | Tunac . |

FOREIGN PATENT DOCUMENTS 1413545  11/1964  France ................................ 215/1 C Primary Examiner—Larry Jones
Attorney, Agent, or Firm—Harness, Dickey & Pierce

[57] ABSTRACT

A culture vessel for improving culture or cell yield of anchored cell or suspension cultures has a fluted body wall to provide the vessel with internal ribbing. The internal ribbing of the vessel increases the surface area available for anchorage-competent cell growth and also enhances the agitation of cells in suspension culture to disperse the cells and promote growth.

21 Claims, 5 Drawing Sheets

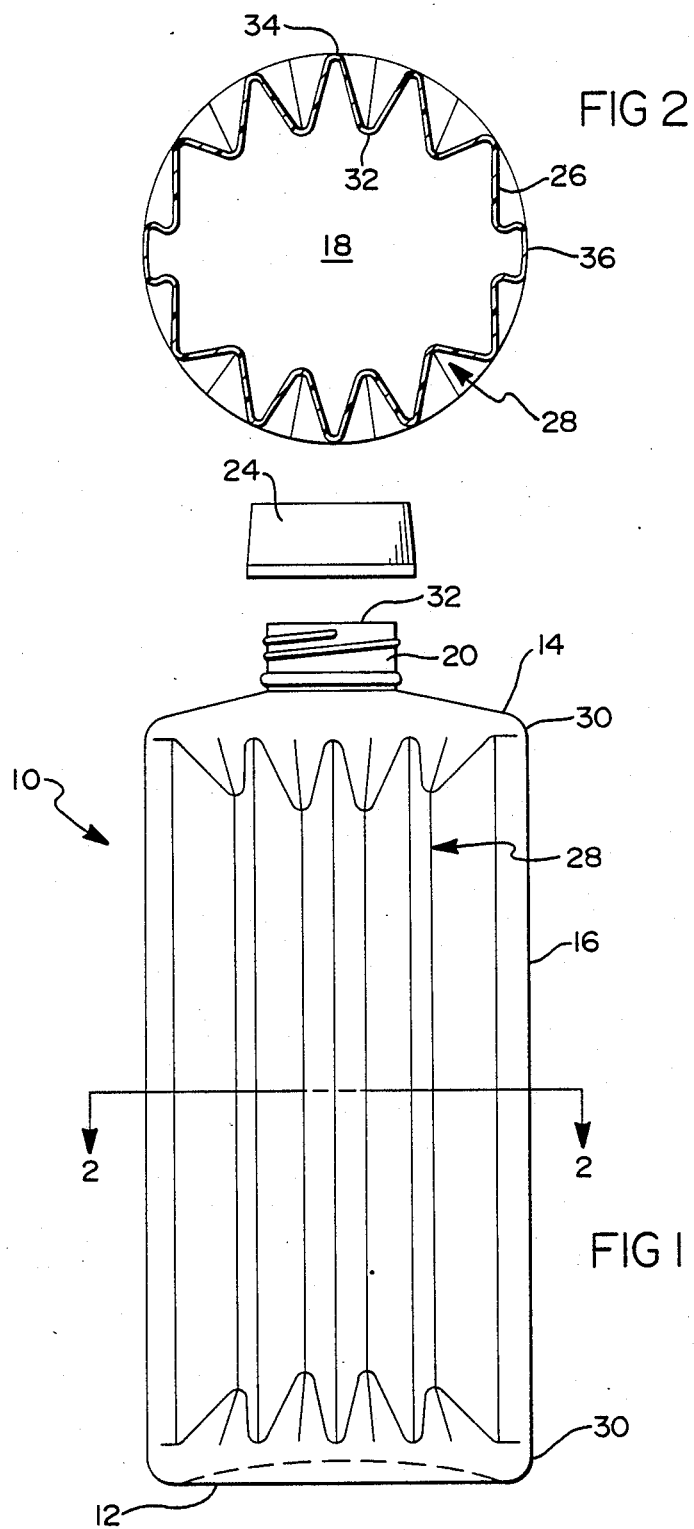

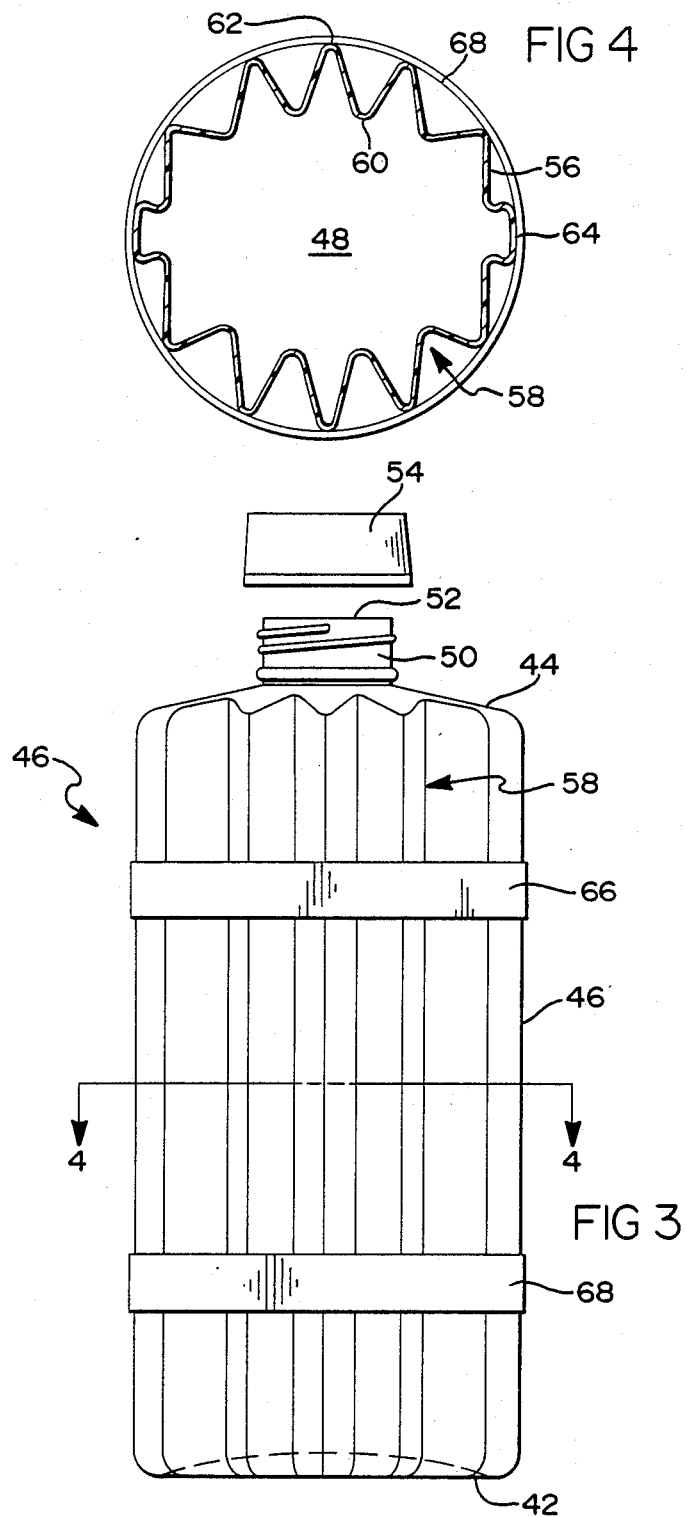

FLUTED CULTURE VESSEL

BACKGROUND OF THE INVENTION

The present invention relates generally to cell culture, and, more particularly, to a fluted culture vessel for both anchored cell and suspension culture.

Oftentimes, it is desirable to grow large amounts of cells primarily for cell by-products, such as insulin, interferon, urokinase or viral vaccines. Simply increasing the number of culture vessels or units to increase the number of cells in culture is not, however, always a practical solution. Culturing, particularly in roller bottles, is expensive, labor-intensive and requires significant capital outlay for equipment such as incubators and rotating apparatuses. Furthermore, simply using a higher number of vessels increases the degree of handling, and thus, the risk of contamination and damage of the vessel and its contents.

One alternative to increasing the number of vessels has been to modify the vessel itself to improve the culture or cell yield per vessel, thereby also increasing the yield of any desired cell by-product. The extent to which a culture vessel can be modified, however, is limited by several factors. For example, a vessel's size and configuration is generally limited by the manufacturing processes and materials employed in its construction. Modifications of the vessel exterior are also usually restricted to those which will fit conventional laboratory equipment such as rotation apparatuses, incubators, and standard agitators, stirrers or shakers. Thus, most modifications have generally been confined to the modification of the vessel's interior growth chamber.

The modification of growth chambers of vessels used for anchored cell culture has been primarily directed to increasing the surface area available for cell attachment and growth. This increase in surface area has been accomplished by the use of various inserts, such as spirals and cell beads, in conjunction with the vessel. However, these methods have several disadvantages, including cost, increased labor, and additional handling Additional handling is particularly undesirable because it increases the risk of contamination and possible exposure of the handler to hazardous materials if such materials are being used in the culture process.

With respect to vessels used for suspension culture, their interior growth chambers have been modified to help disperse and enhance the growth of cells in suspension. Such modifications have resulted in conventional baffled flasks, and the radially-baffled bottle disclosed in U.S. Pat. No. 4,665,035 issued May 12, 1987 to Tunac. However, these vessels are generally adapted only for microbial or suspension culture and are not useful for both anchorage-competent and anchorage-independent cell growth.

Thus it would be desirable to provide a universal culture vessel which can improve the culture or cell yield per unit for either anchored cell or suspension culture, which does not require additional handling and which can fit standard laboratory equipment.

SUMMARY OF THE INVENTION

The present invention provides a fluted culture vessel which can be used to increase the culture or cell yield per unit for either anchored cell or suspension culture, does not require additional handling, and can be inexpensively manufactured to fit standard external dimensions. By the phrase "increase in culture or cell yield", as used herein, is meant an increase in the number of cells or viable cells or their byproducts per culture vessel or unit.

The fluted vessel of the present invention generally comprises a base and top and a body portion integral therewith defining an interior growth chamber. The wall of the body portion of the vessel is fluted along a substantial portion of its length, thus ribbing the interior and exterior surfaces of the body wall of the vessel. With respect to anchored cell culture, ribbing of the interior of the vessel increases the surface area available for attachment and growth of anchorage-competent cells, thus increasing the culture or cell yield per vessel. With respect to suspension culture, the interior ribbing of the vessel of the invention enhances agitation of the culture in suspension to help disperse the cells and promote growth of the culture.

The vessel of the present invention is universal in that it can be used for both anchored cell culture of anchorage-competent cells and suspension culture of anchorage-independent cells. As used herein, the term "anchorage-competent" cells refers both to cells such as anchorage-dependent cells which require a support surface for growth, and cells which do not require but are capable of growing on a support surface. By "anchorage-independent" cells is meant those cells or organisms which are capable of growth in suspension.

In addition, the vessel of the invention can be used as either an open or closed culture system, as well as a fermentation system. Closed culture systems, as defined herein, are those culture systems which are closed to the external atmospheric environment, for example, screw-capped roller bottles. Open culture systems permit gaseous exchange with the external atmosphere and culture conditions can be regulated, for example, by control of the external atmospheric environment (e.g. $CO_2$ incubation or buffering). Fermentation systems combine features of both open and closed systems, feeding external gases into a closed system and regulating the internal atmospheric environment by external modulation.

These and further advantages of the fluted vessel of the present invention will become apparent upon a further reading of the detailed description of the preferred embodiments taken in conjunction with the drawings.

BRIEF DESCRIPTION OF THE DRAWINGS

FIG. 1 is a elevational side view of a preferred embodiment of a fluted vessel of the present invention.

FIG. 2 is a cross-sectional view taken along line 2—2 in FIG. 1.

FIG. 3 is a side elevational view of another preferred embodiment of a fluted vessel of the present invention.

FIG. 4 is a cross-sectional view taken along line 4—4 in FIG. 3.

DETAILED DESCRIPTION OF THE PREFERRED EMBODIMENTS

Figure 6:
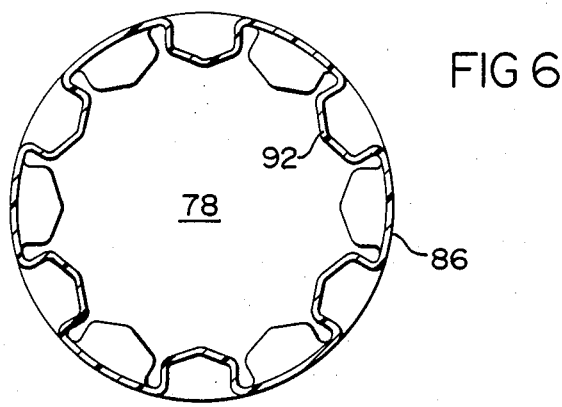
FIG. 6 is a cross-sectional view taken along line 6—6 in FIG. 5.

Referring first to FIGS. 1 and 2, a fluted vessel of the present invention is shown and denoted generally by the reference numeral 10. Vessel 10 generally comprises a generally circular base portion 12, a generally circular top portion 14 remote from said base portion 12, and a generally cylindrical body portion 16 unitary with base and top portions 12 and 14, said portions defining an interior growth chamber 18. Vessel 10 further comprises neck 20 unitary with top portion 14 which defines an opening 22 into said growth chamber 18. Vessel 10 preferably further includes a cap 24 adapted to fit neck portion 20. Preferably the exterior of neck 20 and interior of cap 24 are threaded to permit cap 24 to be tightened onto neck 20 should a closed culture system be desired. Vessel 10 or cap 24 of vessel 10 may further be provided with pressure release means (not shown) to release gas pressure during closed or fermentation culture.

Body portion 16 generally comprises a body wall 26 roughly cylindrical at its outermost circumference. As shown in FIGS. 1 and 2, a substantial portion of the length of body wall 26 is longitudinally fluted to form a plurality of relatively evenly-spaced substantially V-shaped grooves or channels 28. However, as shown in FIG. 1, the upper and lower ends of body wall 26 are not fluted in order to provide exterior grip points 30 for the rollers of a rotary apparatus. Such grip points may become particularly important if the vessel is used for anchored cell culture. Generally, in anchored cell culture, a roller bottle is placed on its side on a rotating apparatus to gently rotate the vessel and its contents during culture. Thus, grip points 30 will facilitate rotation of the vessel by providing the rollers with a surface for gripping the vessel.

As shown particularly in the cross-sectional view of FIG. 2, channels 28 create substantially V-shaped internal ribbing 32 and external ribbing 34 of body wall 26. Preferably, however, a pair of opposing external ribs are rounded or squared off at their outermost portions to define a set of opposing generally U-shaped external grip ribs 36 to facilitate gripping and handling of the culture vessel 10. The flattened portion of the ribs further provides a convenient surface for writing on or marking the vessel exterior.

Referring now to FIGS. 3 and 4, another preferred embodiment of a culture vessel of the invention is shown and indicated by the numeral 40. Vessel 40 also comprises a generally circular base portion 42, a generally circular top portion 44 remote from said base portion 42 and a generally circular body portion 46 unitary with the base and top portions 12 and 14, said portions defining an interior growth chamber 48. Vessel 40 further comprises a neck 50 unitary with top portion 44 which defines an opening 52 into said growth chamber 48. Vessel 40 also preferably further includes a cap 54 adapted to fit neck portion 50, and the exterior of neck 50 and interior of cap 54 are preferably threaded to permit cap 54 to be tightened onto neck 50 should a closed culture system be desired.

Body portion 46 generally comprises a body wall 56 roughly cylindrical at its outermost circumference. As shown in FIGS. 3 and 4, body wall 56 of body portion 46 is longitudinally fluted along approximately all of its length by a plurality of relatively-evenly spaced substantially V-shaped grooves or channels 58. As best shown in FIG. 4, channels 58 create substantially V-shaped internal 60 and external 62 ribbing of body wall 56. Preferably, however, a pair of opposing external ribs 64 are rounded or squared off at their most exterior portion to provide a set of opposing grip ribs on the exterior surface of body wall 56 to facilitate the handling of vessel 40.

Referring again to FIG. 3, vessel 40 is also preferably provided with upper and lower collars, 66 and 68 respectively, which encircle the exterior surface of each end of body wall 56 of body portion 46. Collars 66, 68 are provided to create or maximize the vessel's grip point should vessel 40 be placed on its side on the rollers of a rotating apparatus. Collars 66, 68 can be constructed of any suitable material such as rubber, plastic, or any other elastic or pliable material. Although collars 66, 68 may be affixed to vessel 40, they are preferably removable from the vessel's surface so that they can be used or removed at the user's option.

Figure 5:
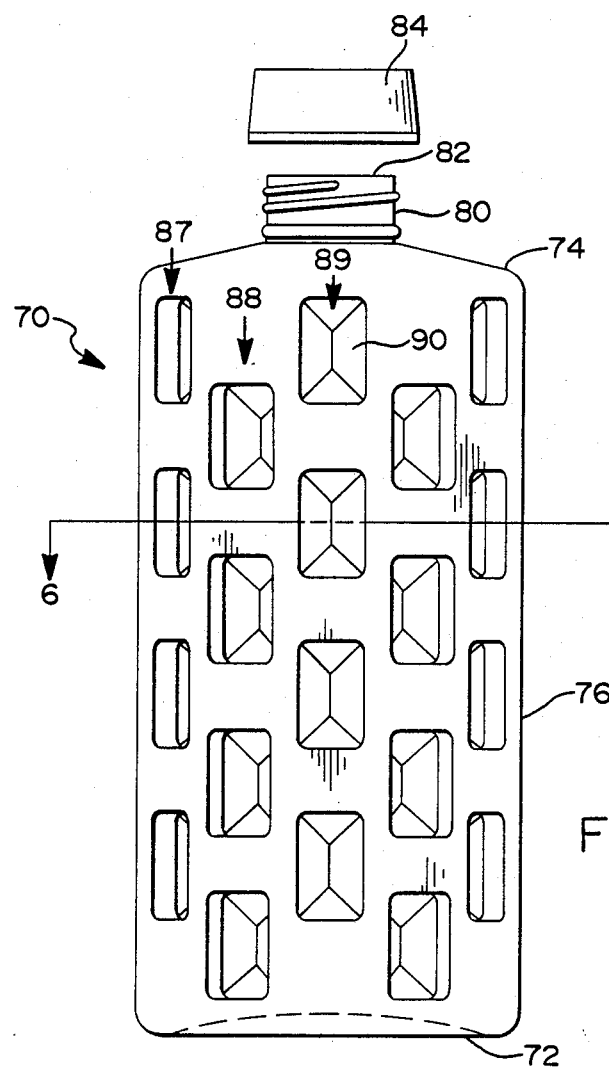
FIG. 5 is a side elevational view of another preferred embodiment of a fluted vessel of the present invention.

FIGS. 5 and 6 illustrate another preferred embodiment of the fluted vessel of the invention indicated by the numeral 70. Vessel 70 again comprises a generally cylindrical base portion 72, a generally cylindrical top portion 74 remote from said base portion 72 and a generally cylindrical body portion 76 unitary with base and top portions 72 and 74, said portions defining an interior growth chamber 78. Vessel 70 further comprises neck portion 80, unitary with top portion 74 and which defines an opening 82 into said interior growth chamber. Vessel 70 preferably also includes a cap 84 adapted to fit neck portion 80.

As shown in FIG. 5, body portion 76 of vessel 70 comprises a body wall 86 which includes a series of longitudinal rows indicated by 87, 88, 89 of generally trough-shaped discrete flutes 90. Thus, as shown in the cross-section view of FIG. 6, the interior surface of body wall 86 includes longitudinal rows of generally V-shaped discrete ribs 92 defined by the exterior flutes 90. Referring again to FIG. 5, flutes 90, and therefore discrete internal ribs 92, within each row are preferably horizontally staggered with respect to the flutes of adjacent rows as shown at rows 87, 88, 89. Thus, when a culture vessel containing medium or other liquid contents is rotated about its longitudinal axis, such staggering of the internal ribs 92 provides a paddle wheel effect to agitate the contents of the vessel.

Figure 8:
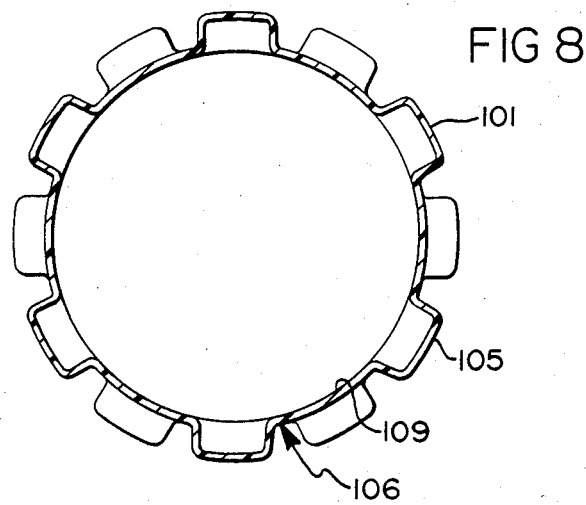
FIG. 8 is a cross-sectional view taken along line 8—8 in FIG. 8.
Figure 7:
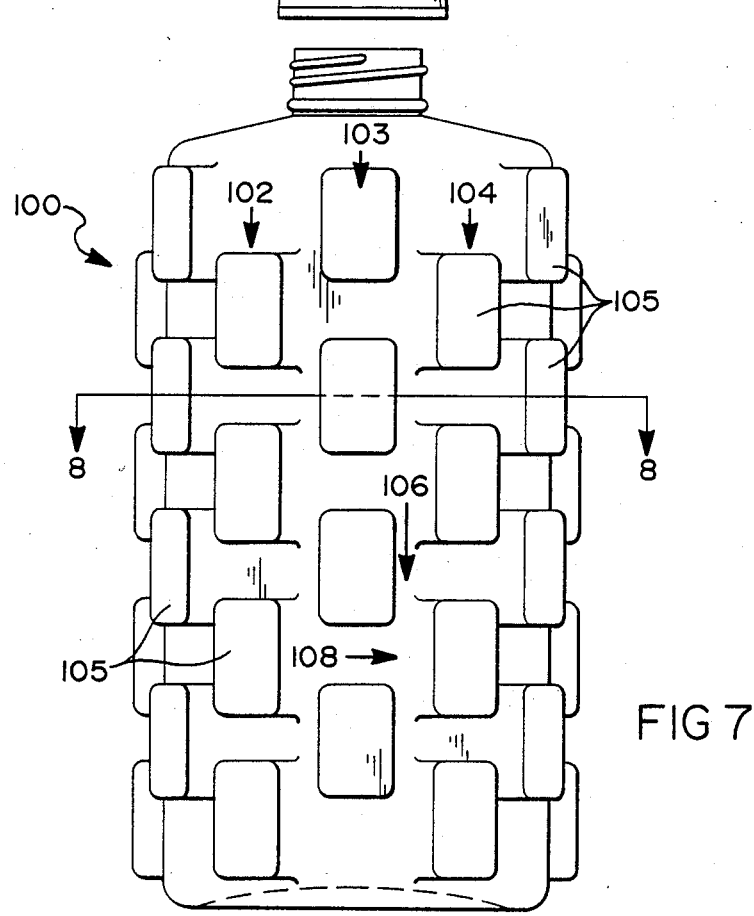
FIG. 7 is a side elevational view of another preferred embodiment of the fluted vessel of the present invention.

FIGS. 7 and 8 depict yet another preferred embodiment of the fluted vessel of the invention indicated by the numeral 100. Vessel 100 is similar to the vessels depicted in FIGS. 1-6 except for the configuration of its fluting. In vessel 100 body wall 101 of vessel 100 includes longitudinal rows, for example, 102, 103, 104, of external rectangularly-shaped discrete ribs 105, the external ribs of each row being horizontally staggered with respect to the exterior ribs of adjacent rows. The configuration of such external ribbing 105 thus flutes the external body wall 101 in a lattice-like configuration. This lattice-like fluting includes longitudinally extending flutes, as at 106, between external rib rows which are cross-connected by horizontal fluting, as at 108, occurring between adjacent ribs of a row. The latticed fluting of the exterior of body wall 101 in turn defines a corresponding lattice-like internal ribbing 109, with longitudinally-extending internal ribs defined by the longitudinally-extending exterior fluting between the external rib rows and cross-connecting internal ribs defined by the fluting occurring between adjacent external ribs within a row.

Figure 9:
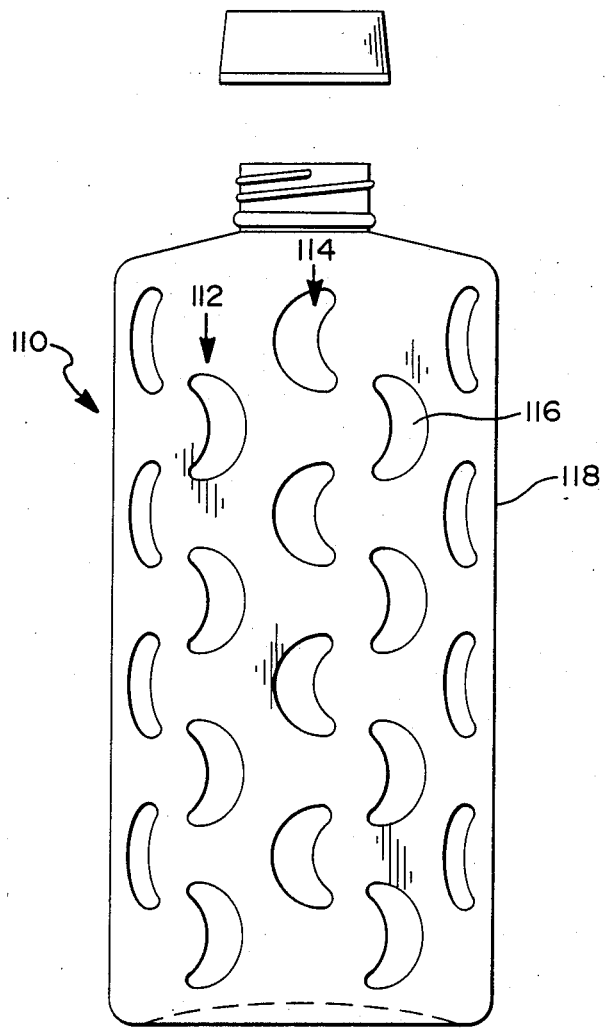
FIG. 9 is a side elevational view of still another preferred embodiment of the fluted vessel of the present invention.

Referring now to FIG. 9, still another preferred embodiment of a fluted vessel of the present invention is shown and indicated by the numeral 110. Vessel 110 of FIG. 9 is also similar to the vessels shown in FIGS. 1–8, but has an alternative fluting configuration. The fluting of vessel 110 comprises adjacent longitudinal rows for example, at 112 and 114, of crescent-shaped flutes 116 molded into body wall 118, which in turn, define internal rows of crescent-shaped ribs extending into the interior growth chamber. Preferably, the arcs of adjacent rows of crescent flutes are reversed and the flutes of adjacent rows horizontally staggered with respect to one another to enhance agitation of the vessel contents, should such agitation be desired.

The fluted vessel of the present invention is preferably manufactured so that the outermost circumference and length of the vessel are within standard dimensions to ensure compatibility with currently available laboratory equipment. It should be appreciated, however, that the size and shape of the vessel of the invention may be varied to suit specific needs. Moreover, it should also be appreciated that the fluting of the vessel may vary in size and configuration and a combination of different fluting configurations may be employed within a single vessel.

Suitable materials for the vessel of the invention are materials which are biologically-compatible with cells in culture, resistant to the chemicals used in culture, and which can be molded or fluted to provided a ribbed interior surface. It is preferred that the material of the vessel of the invention also be capable of supporting anchored cell culture. However, it should be appreciated that if the vessel is to be used strictly for suspension culture, the material employed in its construction need not support anchored cell attachment and growth. Preferably, the material should also be transparent to permit visual inspection of the vessel contents without their removal, although color additives may be used to, for example, increase UV shielding of the culture.

Suitable materials for the vessel of the invention include glass, polystyrene and other transparent polymeric resins. A preferred material is polyethylene terephthalate and its derivatives which can be easily and inexpensively molded into a fluted configuration in accordance with the principles of the invention. Polyethylene terephthalate and its derivatives are also preferred because they can be used for either suspension or anchored cell culture. As a cell support surface for anchored cell culture, polyethylene terephthalate exhibits adequate cell attachment and release properties without pretreatment of the surface prior to culture to enhance or reduce cell attachment or release.

In addition, polyethylene terephthalate, particularly with certain additives such as glycol, is highly shatter-resistant. Polyethylene terephthalate and its derivatives also exhibit adequate gas barrier properties and a high degree of creep resistance which can be important when the vessel is employed as a closed culture system.

It will be appreciated that the above-disclosed embodiments are well-calculated to achieve the aforementioned objectives of the present invention. In addition, it is evident that those skilled in the art, once given the benefit of the foregoing disclosure, may now make modifications of the specific embodiments described herein without departing from the spirit of the present invention. Such modifications are to be considered within the scope of the present invention, which is solely limited by the scope and spirit of the appended claims.

What is claimed is:

1. An improved culture vessel for increasing culture or cell yield comprising:
a base portion, a top portion remote from said base portion, and a body portion unitary with said base and top portions, said portions defining an interior growth chamber adapted for the culture of cells, said top portion further including a neck portion defining an opening into said growth chamber, and said body portion further including a body wall with interior and exterior surfaces, said vessel further comprising a plurality of longitudinal rows of ribbing extending into said growth chamber from and unitary with said interior surface of said body wall, said rows extending along a substantial portion of said body wall, wherein said vessel is comprised of material which is biologically-compatible with cells in culture.

2. The vessel of claim 1, wherein said interior surface of said body wall is adapted for the culture of anchorage-competent cells directly thereon.

3. The vessel of claim 1, wherein each of a majority of said plurality of said longitudinal rows of said ribbing comprises a contiguous rib.

4. The vessel of claim 3, further comprising a collar encircling the outer circumference of said body portion.

5. The vessel of claim 3, wherein a majority of said contiguous ribs are substantially V-shaped in configuration.

6. The vessel of claim 3, wherein said outer surface of said body wall includes at least one external grip rib.

7. The vessel of claim 3, wherein said ribbing further includes connecting ribs connecting adjacent contiguous ribs.

8. The vessel of claim 4, wherein said collar is removable from said outer surface of said body wall and said collar is comprised of pliant material.

9. The vessel of claim 8, wherein each of a majority of said plurality of said longitudinal rows of said ribbing comprises a contiguous rib.

10. The vessel of claim 8, wherein a majority of said plurality of said longitudinal rows of said ribbing comprises a series of discrete ribs.

11. The vessel of claim 1, wherein each of a majority of said plurality of said longitudinal rows of said ribbing comprises a series of discrete ribs.

12. The vessel of claim 11, wherein said discrete ribs within at least one of said longitudinal rows of said ribbing are in staggered arrangement with respect to the discrete ribs of an adjacent row of said ribbing.

13. The vessel of claim 1, wherein said vessel is comprised of a moldable transparent polymeric resin which is biologically-compatible with cells in culture.

14. The vessel of claim 13, wherein said discrete ribs are generally V-shaped.

15. The vessel of claim 13, wherein said discrete ribs are generally quadrangular in shape.

16. The vessel of claim 13, wherein said discrete ribs are generally crescent-shaped.

17. The vessel of claim 1, wherein said vessel is comprised of polyethylene terephthalate.

18. The vessel of claim 1, further comprising closure means for said neck portion for providing a closed culture system.

19. A fluted culture vessel comprising:

a base and body portion integral therewith defining an interior growth chamber adapted for cell culture and having an opening to said growth chamber, said body portion having a body wall having an inner and outer surface, said wall having fluting molded therein, wherein said fluting defines ribbing on said inner surface of said body wall, said ribbing further comprising a plurality of rows of ribbing, said rows extending longitudinally along a substantial portion of said body wall, wherein said vessel is comprised of material which is biologically-compatible with cells in culture.

20. A culture system comprising:

a vessel having a base portion, top portion remote from said base portion, and a body portion integral with said base and top portions, said portions defining an interior growth chamber adapted for the culture of cells, said top portion further including a neck portion defining an opening into said growth chamber, and said body portion comprising a body wall with interior and exterior surfaces, said interior surface of said wall having a plurality of longitudinal rows of ribbing extending therefrom, said rows of said ribbing extending along a substantial portion of said body wall, cells located within said vessel, and biologically-compatible medium in contact with said cells within said vessel.

21. A method for increasing culture or cell yield comprising:

providing a culture vessel comprising a base portion, a top portion remote from said base portion, and a body portion unitary with said base and top portions, said portions defining an interior growth chamber adapted for the cutlure of cells, said top portion further including a portion defining an opening into said growth chamber, and said body portion further including a body wall with interior and exterior surfaces, said vessel further comprising a plurality of longitudinal rows of ribbing extending into said growth chamber from said interior surface of said body wall, said rows extending along a substantial portion of said body wall;

providing cell culture medium within said vessel; and inoculating said vessel with cells to be cultured therein.

* * * * *